(12) United States Patent
Li et al.

(10) Patent No.: US 6,512,950 B2
(45) Date of Patent: Jan. 28, 2003

(54) METHODS FOR DELIVERING AGENTS USING ALTERNATING CURRENT

(75) Inventors: S. Kevin Li, Salt Lake City, UT (US); William I. Higuchi, Salt Lake City, UT (US); Honggang Zhu, Salt Lake City, UT (US); Yang Song, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 66 days.

(21) Appl. No.: 09/783,138

(22) Filed: Feb. 13, 2001

(65) Prior Publication Data

US 2001/0044592 A1 Nov. 22, 2001

Related U.S. Application Data

(60) Provisional application No. 60/184,119, filed on Feb. 18, 2000, and provisional application No. 60/244,116, filed on Oct. 28, 2000.

(51) Int. Cl.$^7$ ................................................. A64B 5/05
(52) U.S. Cl. .......................................... 604/20; 108/803
(58) Field of Search ............................ 604/20; 128/803

(56) References Cited

U.S. PATENT DOCUMENTS

| | | | |
|---|---|---|---|
| 3,991,755 A | 11/1976 | Vernon et al. | |
| 4,141,359 A | 2/1979 | Jacobsen et al. | |
| 4,325,367 A | 4/1982 | Tapper | |
| 4,340,047 A | 7/1982 | Tapper et al. | |
| 4,406,658 A | 9/1983 | Lattin et al. | |
| 4,689,039 A | 8/1987 | Masaki | |
| 4,702,732 A | * 10/1987 | Powers et al. | 604/20 |
| 4,734,090 A | 3/1988 | Sibalis | |
| 4,752,285 A | 6/1988 | Petelenz et al. | |
| 4,764,164 A | 8/1988 | Sasaki | |
| 4,786,278 A | 11/1988 | Masaki | |
| 4,792,702 A | 12/1988 | Masaki | |
| 4,850,956 A | 7/1989 | Bontemps | |
| 4,931,046 A | 6/1990 | Newman | |
| 5,002,527 A | 3/1991 | Reller et al. | |
| 5,006,108 A | 4/1991 | LaPrade | |
| 5,013,293 A | 5/1991 | Sibalis | |
| 5,019,034 A | 5/1991 | Weaver et al. | |
| 5,023,085 A | 6/1991 | Francoeur et al. | |
| 5,036,861 A | 8/1991 | Sembrowich et al. | |

(List continued on next page.)

FOREIGN PATENT DOCUMENTS

| | | |
|---|---|---|
| DE | 41 37 960 A1 | 5/1993 |
| EP | 0 254 166 A2 | 1/1988 |
| EP | 0 266 083 A1 | 5/1988 |

(List continued on next page.)

OTHER PUBLICATIONS

Ll, et al., Pore Induction in Human Epidermal Membrane During Low to Moderate Voltage Iontophoresis: A Study Using AC Iontophoresis, *Journal of Pharmaceutical Sciences*, vol. 88, No. 4, pp. 419–427.

(List continued on next page.)

*Primary Examiner*—Philippe Derakshani
(74) *Attorney, Agent, or Firm*—Townsend and Townsend and Crew LLP (57) ABSTRACT

A variety of methods for transporting different agents such as pharmaceutical agents, nutrients and genetic materials across a tissue are provided. The methods utilize an AC signal to maintain a substantially constant electrical state in a region of the tissue through which transport occurs, thereby allowing agent to be transported across the tissue in a controlled and predictable manner. Certain methods include an optional AC or DC prepulse signal to initially achieve the target electrical state. An optional DC offset signal can also be included to assist in promoting transfer of the agent. The methods have utility in a variety of different clinical settings and applications.

53 Claims, 5 Drawing Sheets

U.S. PATENT DOCUMENTS

| | | | |
|---|---|---|---|
| 5,042,975 A | 8/1991 | Chien et al. | |
| 5,047,007 A | 9/1991 | McNichols et al. | |
| 5,056,521 A | 10/1991 | Parsons et al. | |
| 5,057,072 A | 10/1991 | Phipps | |
| 5,135,478 A * | 8/1992 | Sibalis | 604/20 |
| 5,140,985 A | 8/1992 | Schroeder et al. | |
| 5,213,568 A | 5/1993 | Lattin et al. | |
| 5,224,927 A * | 7/1993 | Tapper | 604/20 |
| 5,279,543 A | 1/1994 | Glikfeld et al. | |
| 5,312,325 A | 5/1994 | Sibalis | |
| 5,314,502 A | 5/1994 | McNichols et al. | |
| 5,318,514 A | 6/1994 | Hofmann | |
| 5,328,452 A | 7/1994 | Sibalis | |
| 5,328,453 A | 7/1994 | Sibalis | |
| 5,328,454 A | 7/1994 | Sibalis | |
| 5,336,168 A | 8/1994 | Sibalis | |
| 5,362,307 A | 11/1994 | Guy et al. | |
| 5,372,579 A | 12/1994 | Sibalis | |
| 5,391,195 A | 2/1995 | Van Groningen | |
| 5,395,310 A | 3/1995 | Untereker et al. | |
| 5,405,317 A | 4/1995 | Myers et al. | |
| 5,415,629 A | 5/1995 | Henley | |
| 5,421,817 A | 6/1995 | Liss et al. | |
| 5,423,739 A | 6/1995 | Phipps et al. | |
| 5,443,441 A | 8/1995 | De Claviere | |
| 5,465,713 A | 11/1995 | Schoendorfer | |
| 5,499,967 A | 3/1996 | Teillaud et al. | |
| 5,538,503 A | 7/1996 | Henley | |
| 5,571,149 A | 11/1996 | Liss et al. | |
| 5,617,851 A | 4/1997 | Lipkovker | |
| 5,620,580 A | 4/1997 | Okabe et al. | |
| 5,645,526 A | 7/1997 | Flower | |
| 5,658,247 A | 8/1997 | Henley | |
| 5,667,487 A | 9/1997 | Henley | |
| 5,676,144 A | 10/1997 | Schoendorfer | |
| 5,722,397 A | 3/1998 | Eppstein | |
| 5,730,714 A | 3/1998 | Guy et al. | |
| 5,771,890 A | 6/1998 | Tamada | |
| 5,817,012 A | 10/1998 | Schoendorfer | |
| 5,827,181 A | 10/1998 | Dias et al. | |
| 5,885,211 A | 3/1999 | Eppstein et al. | |
| 5,899,876 A | 5/1999 | Flower | |
| 5,911,223 A | 6/1999 | Weaver et al. | |
| 5,928,571 A | 7/1999 | Chan | |
| 5,944,662 A | 8/1999 | Schoendorfer | |
| 5,947,921 A | 9/1999 | Johnson et al. | |
| 5,954,685 A | 9/1999 | Tierney | |
| 5,968,006 A | 10/1999 | Hofmann | |
| 5,978,701 A | 11/1999 | Johnson et al. | |
| 5,983,131 A | 11/1999 | Weaver et al. | |
| 5,989,409 A | 11/1999 | Kurnik et al. | |
| 5,991,655 A | 11/1999 | Gross et al. | |
| 5,997,501 A | 12/1999 | Gross et al. | |
| 6,006,130 A | 12/1999 | Higo et al. | |
| 6,010,613 A | 1/2000 | Walters et al. | |
| 6,018,679 A | 1/2000 | Dinh et al. | |
| 6,023,629 A | 2/2000 | Tamada | |
| 6,041,252 A | 3/2000 | Walker et al. | |
| 6,041,253 A | 3/2000 | Kost et al. | |
| 6,048,337 A | 4/2000 | Svedman | |

FOREIGN PATENT DOCUMENTS

| | | |
|---|---|---|
| EP | 0 308 572 A2 | 3/1989 |
| EP | 0 468 636 A1 | 1/1992 |
| EP | 0 847 775 A1 | 6/1998 |
| GB | 2 177 928 A | 2/1987 |
| JP | 409276416 A | 10/1977 |
| JP | 402124176 A | 5/1990 |
| JP | 402243168 A | 9/1990 |
| JP | 403045272 A | 2/1991 |
| JP | 405049702 A | 3/1993 |
| JP | 407067971 A | 3/1995 |
| JP | 408052224 A | 2/1996 |
| JP | 408322948 A | 12/1996 |
| JP | 411019226 A | 1/1999 |
| WO | WO 88/00846 A1 | 2/1988 |
| WO | WO 91/15256 A1 | 10/1991 |
| WO | WO 91/15257 A1 | 10/1991 |
| WO | WO 92/18197 A1 | 10/1992 |
| WO | WO 94/05368 A1 | 3/1994 |
| WO | WO 94/28967 A1 | 12/1994 |
| WO | WO 97/07853 A1 | 3/1997 |
| WO | WO 98/14235 A1 | 4/1998 |
| WO | WO 99/30773 A1 | 6/1999 |
| WO | WO 99/43383 A1 | 9/1999 |
| WO | WO 99/52589 A1 | 10/1999 |

OTHER PUBLICATIONS

Dalziel, et al., Let–Go Currents and Voltages, *AIEE Transactions*, vol. 75, May 1956.

Dalziel, et al., Effect of Frequency On Perception Currents, *AIEE Transactions*, vol. 69, 1950, pp. 1162–1168.

Higuchi, et al., Mechanistic Aspects of Iontophoresis In Human Epidermal Membrane, *Journal of Controlled Release*, 62 (1999), pp. 13–23, Elsevier Science B.V.

Sharma, et al., Transdermal Drug Delivery Using Electroporation. II. Factors Influencing Skin Reversibility In Electroporative Delivery of Terazosin Hydrochloride in Hairless Rats, *Journal of Pharmaceutical Sciences*, vol. 89, No. 4, Apr. 2000, pp. 536–544, Wiley–Liss, Inc,. and American Pharmaceutical Association.

Kim, et al., Convective Solvent Flow Across the Skin During Iontophoresis, *Pharmaceutical Research*, vol. 10, No. 9, pp. 1315–1319, 1993, Plenum Publishing Corporation.

Delgado–Charro, et al., Characterization of Convective Solvent Flow During Iontophoresis, *Pharmaceutical Research*, vol. 11, No. 7, pp. 929–935, 1994, Plenum Publishing Corporation.

Van Der Geest, et al., Iontophoresis of Bases, Nucleosides, and Nucleotides, *Pharmaceutical Research*, vol. 13., No. 4, pp. 553–558, 1996, Plenum Publishing Corporation, 1996.

Peck, et al., Flux Enhancement Effects of Ionic Surfactants Upon Passive and Electroosmotic Transdermal Transport, *Journal of Pharmaceutical Sciences*, vol. 87, No. 9, pp. 1161–1169, Sep. 1998, American Chemical Society and American Pharmaceutical Association, 1998.

Ll, et al., Lag Time Data for Characterizing the Pore Pathway of Intact and Chemically Pretreated Human Epidermal Membrane, *International Journal of Pharmaceutics*, 170, pp. 93–108, 1998, USA.

Ll, et al., Pore Charge Distribution Considerations In Human Epidermal Membrane Electroosmosis, *Journal of Pharmaceutical Sciences*, vol. 88, No. 10, pp. 1044–1049, American Chemical Society and American Pharmaceutical Association, 1999.

Ll, et al., Characterization of the Transport Pathways Induced During Lower to Moderate Voltage Iontophoresis in Human Epidermal Membrane, *Journal of Pharmaceutical Sciences*, vol. 87, No. 1, pp. 40–48, American Chemical Society and American Pharmaceutical Association, 1998.

Copy of International Search Report for PCT/US 01/04654.

* cited by examiner

METHODS FOR DELIVERING AGENTS USING ALTERNATING CURRENT

CROSS-REFERENCES TO RELATED APPLICATIONS

This application claims the benefit of U.S. Provisional Application No. 60/184,119, filed Feb. 18, 2000, and the benefit of U.S. Provisional Application No. 60/244,116, filed Oct. 28, 2000, both of which are incorporated herein in their entirety for all purposes. This application is also related to U.S. application Ser. No. 09/783,696, filed Feb. 13, 2001, which claims the benefit of U.S. Provisional Application No. 60/244,088, filed Oct. 28, 2000, both of which are also incorporated in their entirety for all purposes.

STATEMENT AS TO RIGHTS TO INVENTIONS MADE UNDER FEDERALLY SPONSORED RESEARCH AND DEVELOPMENT

This invention was made with support from Grant Number GM 43181 awarded by the National Institutes of Health. Therefore, the government has certain rights in this invention.

FIELD OF THE INVENTION

This invention relates generally to the field of drug delivery and more particularly to methods of transport of agents such as pharmaceutically active agents across tissues, including transport by iontophoresis.

BACKGROUND OF THE INVENTION

The transport of various agents such as metabolites, drugs and nutrients across tissues is a function primarily of three factors: tissue permeability, the presence or absence of a driving force and the size of the area through which transport occurs. The lack of inherent permeability for many tissues renders it difficult to move agents across a body surface. Permeability in many tissues is low because cell membranes are generally composed of lipid bilayers that are relatively impermeable to ionized and uncharged polar species. For example, transport of agents across skin has proved difficult in part because the outer layer of skin termed the stratum corneum consists of tightly packed cells with intercellular lipids which severely impede passage of substances through this barrier.

Oral administration of drugs remains the most common method of drug delivery because the cells lining the intestine tend to be quite permeable and because oral ingestion is generally accepted by patients. This approach, however, has a variety of shortcomings including degradation of the agent within the gut, the inability to apply a driving force, and local gastrointestinal irritation.

Iontophoresis is an alternative approach that can be utilized to deliver agents across a tissue by the application of an electrical current. In practice, iontophoretic methods generally involve positioning an electrode that includes some type of reservoir or absorbent pad that contains the agent to be transferred on the tissue through which delivery is to occur. Another electrode that typically does not include the agent but contains, or is coated with, a conductive gel is also placed in contact with the tissue to complete the electrical circuit.

Application of a voltage between the two electrodes and across the tissue generates a current that causes the ionized agent to move towards the electrode of opposite charge, thereby driving the agent through the tissue. Neutral agents can also be transported, albeit less effectively than ionized agents, via electroosmosis. Iontophoresis induces the formation and/or enlargement of pores within tissues, which in turn increase tissue permeability to ionic and polar agents and drive these agents through such pores. When the tissue is skin, the agent penetrates the stratum corneum and passes into the dermo-epidermal layer. The innermost portion of the dermis is typically referred to as the papillary layer and contains a network of capillaries from the vascular system. This network absorbs the agent and subsequently moves it to the main portion of the circulatory system.

A majority of the iontophoretic methods utilize constant-current DC signals to effectuate transport. There are several problems associated with such methods that have resulted in limited acceptance by clinicians, patients and government regulators. One shortcoming of constant-current DC is that the rate of drug delivery changes with the passage of time, even though a constant current is applied. The inability to provide a constant flux at constant current is possibly due to time-dependent changes in tissue porosity, accompanying changes in pore surface charge density and effective pore size over the course of treatment. Such changes pose significant problems in effectively controlling the transdermal delivery of drugs by iontophoresis. It is generally observed that with constant-current DC methods the transference number (fraction of total current carried by a particular charged species) for the bioactive agent increases with time over the course of a typical iontophoresis procedure. This variability in transference number means that the amount of agent transported across a tissue varies with time and cannot be controlled nor predicted effectively.

Problems in controlling the extent of electroporation with constant-current DC methods also result in high inter-and intra-patient variability. Hence, not only does the amount of agent transported vary as a function of time, there is further day-to-day variation for the same individual, as well as variation from person to person.

Yet another problem is a function of byproducts formed during iontophoresis. With many systems, transport is accompanied by water hydrolysis that causes significant pH shifts in the bulk solution and gas formation at the surface of the electrodes. In particular, protons form at the anode while hydroxide ions form at the cathode. Such pH shifts may result in electrochemical burns that can cause tissue damage. In addition, gas formation interferes with the contact, and hence the electrical conduction between the electrode and tissue surface.

Various strategies have been tested to address these problems, including using different waveforms and pulsed DC signals rather than constant-current signals. It has been suggested that the use of pulsed DC signals should theoretically provide improved performance by allowing skin capacitance to discharge, thereby allowing for more controlled current flow and drug delivery. However, many DC pulsed methods suffer from at least some of the same general problems as the constant-current DC methods.

Illustrative of a general pulsed DC method is U.S. Pat. No. 5,019,034 to Weaver et al. Weaver et al. discuss methods that utilize a series of short DC pulses to induce electroporation, in particular a state referred to as reversible electrical breakdown. Various forces can then be utilized to effectuate transport of an agent across a tissue. Once electroporation is established, the nature of the DC pulses (e.g., pulse duration, shape and frequency) is maintained until transfer is complete. U.S. Pat. No. 5,391,195 to Van Groningen discusses a method that uses a pulsed direct current with a frequency of at least 1 kHz and having a duty cycle of at least 80%. Such a signal is asserted to increase the efficiency of transport. Methods employing DC signals and methods designed to monitor the level of current such that a relatively stable current is applied and are discussed in U.S. Pat. No. 4,931, 046 to Newman and U.S. Pat. No. 5,042,975 to Chien et al. Certain DC methods employ a combination of pulsed and continuous electric fields. For example, U.S. Pat. No. 5,968, 006 to Hoffman discusses a system in which one electrode assembly is used to generate a pulsed DC signal to induce pores in a patient's skin. A second electrode assembly generates a low voltage continuous electric field of sufficient magnitude to affect transport of molecules through the electroporated region. Each of the foregoing patents, are limited in that they discuss only the use of direct current to perform iontophoresis. These patents also do not discuss how to maintain a substantially constant electrical state in the electroporated region of the tissue in order to maintain constant transference numbers, and hence constant flux, for the agent(s) being transported.

The iontophoretic literature on balance has taught against the utility of AC signals in conducting iontophoresis. It has been the belief of many of those skilled in the art that an AC signal lacks the necessary driving force to achieve effective iontophoretic transport; instead, the view has been that the driving force of an applied DC signal is required to transport a charged particle. The bidirectional nature of an AC signal, led many to conclude that the use of an AC signal would result in inefficient transport at best, and perhaps no net transfer at all. For example, in U.S. Pat. No. 5,391,195 it is noted that "the negative pulse [reverse pulse of an alternating current] would result in an inverse effect to the positive pulse, thereby reducing the efficiency of treatment."

Nonetheless, certain investigators have discussed the use of AC signals for specific purposes in conducting iontophoresis. For example, several patents to Sabalis (see, e.g., U.S. Pat. Nos. 5,312,325; 5,328,454; 5,336,168; and 5,372, 579) discuss systems in which a current oscillator is utilized to apply periodic electrical variations to the skin of a patient, the goal being to trigger rhythmical variations of the potential and resistance of the skin. Such variations in turn are said to cause electroosmotic streaming of a liquid containing a therapeutic compound into the patient's circulatory system. This type of delivery is said to be in accord with and reinforce the natural biological rhythms of the patient. U.S. Pat. No. 5,328,453 discusses a system in which the direction of current can periodically be reversed to facilitate transport of a primary drug and a counteractor that inhibits blood clotting and enhances circulatory flow. Reversal of polarity is claimed to be efficacious when the primary drug and counteractor are of opposite charge.

Some methods involve application of a series of waveforms that can include an AC component. U.S. Pat. Nos. 5,135,478 and 5,328,452 to Sabalis, for example, discuss iontophoretic methods that include generating a plurality of waveforms that can be separate or overlapping and that can include an AC signal. The duration, repetition rate, shape and harmonic content of each signal are selected to enhance local blood circulation and impede the process of blood coagulation. U.S. Pat. No. 5,421,817 to Liss et al. discusses the use of complex set of overlapping waveforms that includes a carrier frequency and various modulating frequencies that collectively are said to enhance delivery. While allowing for the inclusion of an AC signal in the set of waveforms, Liss et al. reinforced the view that the use of an AC signal is not preferred, noting that a reversal in polarity will "tend to reverse or slow the transdermal delivery of the drug."

There has also been some discussion in the literature regarding the use of AC signals in iontophoresis to minimize the electrochemical burns that can occur with DC methods (see, e.g., Howard et al., (1995) *Arch. Phys. Med. Rehabil.* 76:463–466; and U.S. Pat. No. 5,224,927 to Tapper). The use of AC signals to control and reduce drug induced skin irritation after passive or iontophoretic transport of a drug has also been discussed (see, e.g., U.S. Pat. No. 6,018,679 to Dinh), as has the use of AC signals in related methods such as in the treatment of hyperhidrosis (see, e.g., Reinauer, et al. (1993) *Br. J Derm.* 129:166–169).

However, none of these patents or articles that discuss the use of AC signals fully address the challenge of maintaining a substantially constant electrical state and a substantially constant electroporative state such that transport of an agent across the tissue occurs in a predictable and controlled fashion during the time period for delivery. Nor is there a discussion of methods for reducing intra-and inter-subject variability that plagues many iontophoretic methods.

SUMMARY OF THE INVENTION

Methods for delivering different agents across a tissue utilizing an AC signal are provided. The methods can be utilized to deliver a number of different agents such as pharmaceutical agents, metal ions and nutrients. During the delivery process, the AC signal is used to maintain a substantially constant electrical state in a region of the tissue through which delivery occurs, thereby allowing agents to be transported across the tissue in a controlled and predictable manner. The methods have utility in a wide range of applications. For example, certain methods can be utilized in various therapeutic treatments, in detoxification methods, in pain management and dermatological treatments.

Thus, certain methods more specifically involve delivering an agent across a tissue by supplying one or more electrical signals, one of which is an AC signal that is applied to the tissue. The AC signal is then adjusted so as to maintain a substantially constant electrical state within a region of the tissue, wherein maintenance of the substantially constant electrical state facilitates delivery of the agent. The AC signal is typically adjusted to maintain a substantially constant state of electroporation in the region of the tissue throughout the time period in which the agent is delivered. With some methods, the electrical state that is maintained by the AC signal is an electrical conductance or electrical resistance. The AC signal applied to the tissue can have essentially any waveform. The waveform can be symmetric or asymmetric, thus including square, sinusoidal, saw-tooth, triangular and trapezoidal shapes, for example. The frequency of the AC signal tends to be at least about 1 Hz, although in other instances the frequency is within the range of about 1 Hz to about 1 kHz, about 1 kHz to about 10 kHz, or about 10 kHz to about 30 kHz.

Other delivery methods include an optional electrical prepulse applied to the tissue prior to the AC signal to induce electroporation within the region of the tissue through which delivery is to occur. The prepulse can be either an AC signal or a DC signal. The voltage of the prepulse generally is in the range of about 1 to about 90 V, in other instances about 9 to about 30 V, in still other instances about 30 to about 40 V, and in yet other instances about 40 to about 90 V. The actual voltage can be any particular voltage or range of voltages within these ranges.

Delivery of the agent across the tissue can be via passive diffusion through an electroporated region induced by the AC signal. Certain methods, however, utilize an optional DC offset signal applied in combination with the AC signal. The DC offset signal is effective to promote delivery of the agent through the region maintained at a substantially constant electrical state. The DC offset signal is typically applied substantially continuously during delivery of the agent and is of a voltage or current effective to control the rate of delivery. The DC offset signal is usually in the range of about 0.1 to 5 V and about 0.01 to 0.5 $mA/cm^2$, but can include any particular voltage, current or range of voltages or currents within this range. In certain methods, the DC offset signal is applied utilizing two electrodes in contact with the tissue and the direction of current flow of the DC offset signal is periodically reversed between the two electrodes.

Still other methods combine both the prepulse and the DC offset with the AC signal to deliver agents across a tissue. Such methods generally involve applying the electrical prepulse to the tissue prior to the AC signal to induce electroporation within the region. The DC offset signal is also applied to the tissue and is effective to promote delivery of the agent through the region maintained at a substantially constant electrical state by the AC signal.

The methods can be utilized with a variety of different types of tissue, including both animal and plant tissues. The tissues can be part of a body surface or artificial. Usually the tissue is skin or mucosal tissue, particularly human skin or mucosal tissue. A variety of agents can also be delivered, including charged and uncharged agents.

DETAILED DESCRIPTION

I. Definitions

Before describing the present invention in detail, it is to be understood that unless otherwise indicated this invention is not limited to specific iontophoretic delivery devices, therapeutic agents, or the like, as such can vary. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a pharmacologically active agent" includes a mixture of two or more active agents, reference to "a vehicle" includes mixtures of two or more vehicles, and the like.

In describing and claiming the present invention, the following terminology will be used in accordance with the definitions set out below.

The term "body surface" is used to refer to skin or mucosal tissue, including the interior surface of body cavities that have a mucosal lining. The term "skin" should be interpreted as including "mucosal tissue" and vice versa.

A "region" of a tissue refers to the region of a tissue that is electroporated via the application of one or more electrical signals and through which the agent is transported. Thus, a region of a body surface refers to an area of skin or mucosal tissue through which an active agent is delivered.

The term "electroporation" generally refers to an increase in tissue permeability believed to be due to pore induction and/or increase in pore size of induced or existing pores through which a substance can be extracted during an iontophoretic process. Thus, the term "electroporative state" refers to the permeability of a tissue that has been electroporated.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The terms "pharmacologically active agent," "pharmaceutical agent," "drug," and "therapeutic agent" are used interchangeably herein to refer to a chemical material or compound suitable for delivery across a tissue (e.g., transdermal or transmucosal administration) and that induces a desired effect. The terms include agents that are therapeutically effective as well as agents that are prophylactically effective. Also included are derivatives and analogs of those compounds or classes of compounds specifically mentioned which also induce the desired effect including active metabolites of the therapeutic agent.

"Vehicles" as used herein refer to carrier materials suitable for administration of an agent across a body surface. Vehicles useful herein include any such materials known in the art, which are nontoxic and do not interact with other components of the pharmaceutical formulation or drug delivery system in a deleterious manner.

By an "effective" amount (or "therapeutically effective" amount) of a pharmacologically active agent is meant a sufficient, but nontoxic amount of the agent to provide the desired effect.

II. Overview

A variety of methods that achieve controlled and predictable transport of agents across tissues are disclosed herein. The methods are based in part upon the recognition that an AC signal alone or in combination with one or more other AC or DC signals can be utilized to induce and maintain a substantially constant electrical state in a region of a tissue through which transport occurs. By maintaining such an electrical state, one can maintain the permeability of the tissue within the region such that pore size, pore density and surface charge density of pores within the region is kept constant. The process of applying an electrical signal to create new pores or enlarge existing pores within a tissue is referred to as electroporation, and the degree of permeability so obtained referred to as the state of electroporation.

Controlling tissue permeability or electroporative state in this manner enables one to reduce variability in the flux of an agent across the tissue such that a constant transference number is achieved for the agent being transported. Reduction in flux variability in turn means that one can deliver agents such as pharmaceuticals in a controlled and predictable way, an aspect that is particularly important for pharmaceuticals having a narrow therapeutic window. Intra- and inter-patient variability in the rate of drug delivery can also be minimized using certain methods disclosed herein.

The electrical state and thus the degree of electroporation of a tissue can be ascertained by monitoring the electrical conductance or resistance of the tissue or similar electrical parameters that correlate with the degree of cell permeability.

While the AC signal is adjusted to maintain a substantially constant electrical state, transport of agent across the tissue can be accomplished in various ways. If the concentration of agent on one side of a tissue is significantly higher than the other side of the tissue (e.g., the exterior side of skin relative to the interior side), transport of an agent through the electroporated region can be achieved by passive Fickian-driven diffusion. Other methods increase the rate of transport by applying a DC offset of the AC signal to the electroporated region to drive the agent through the region.

Certain methods include an optional prepulse to quickly attain a desired electrical state that is then maintained with the AC signal. The prepulse can be either an AC or DC signal. Hence, the methods provided herein can include simply an AC signal ("AC protocol" or "AC-only protocol"), a combination of an AC signal and a DC offset signal ("AC plus DC offset protocol"), either of which can be further combined with an AC or DC prepulse.

The methods provided herein differ significantly from conventional DC or pulsed DC iontophoretic delivery methods. As described in the background section, a significant shortcoming with constant current DC methods and pulsed DC methods is their failure to maintain a constant state of tissue permeability or electroporation. Often the pores within the region of the electroporated tissue change with time during iontophoresis, resulting in a concomitant change in the permeability of the electroporated region. The inability to maintain a substantially constant electroporated state severely limits the ability of constant current DC methods to controllably and predictably deliver an agent across a tissue. The methods of the present invention, by maintaining a substantially constant electrical state during the period in which transfer occurs, can ameliorate this problem.

III. Description of Various Methods

A. General

A common feature of the various methods described herein is the use of an AC signal to maintain a substantially constant electrical state so as to limit flux variability in the transport of agents across a tissue such as a body surface. The electrical state is typically maintained throughout the time period during which transport occurs. By maintaining a substantially constant electrical state and state of electroporation, the effective pore charge density and pore size remain essentially constant during a treatment procedure. This in turn allows for a substantially constant, controllable and determinable transport rate for the agent being delivered.

As used herein, the term "AC signal" generally refers to an electric signal (e.g., current or voltage) that reverses direction periodically. As described further below, typically the AC signal has a frequency of at least about 1 Hz. It should be understood that an AC signal refers not only to signals that reverse direction relative to a zero reference point, but also to signals that are biased relative to a zero reference point. The phrase "electrical state" refers to a state that correlates with or is a measure of the permeability of the tissue in the region being electroporated and that can be measured as an electrical value. A substantially constant electrical state correlates with a substantially constant electroporative state. A substantially constant electrical state is evidenced, for example, by a substantially constant resistance or conductance within the region being electroporated, and/or by a substantially constant transference number (fraction of total current carried by a particular agent) for the agent being transferred.

The methods can be used for the controlled and predictable delivery of various agents, including both charged and uncharged species. As is typical in iontophoresis, the permeant primarily tends to be a charged entity. However, the methods described herein are not limited to the delivery of charged molecules only. Methods set forth herein can be used in the delivery of non-charged agents.

The methods are designed to accomplish delivery of an agent across a tissue and more specifically a region of the tissue. As used herein a "tissue" is defined to mean an aggregation of similar cells and/or cell components united in performance of a particular function. The tissue can be part of a living organism, a section excised from a living organism, or can be artificial. An artificial tissue is one in which an aggregation of cells are grown to function similar to a tissue in a living organism. The aggregated cells, however, are not obtained from a host (i.e., a living organism). Artificial tissues can be grown in vivo or in vitro. Human skin, for instance, can be cultured in vitro to obtain an aggregation of cells, of monolayer thickness or greater, that can function as a skin tissue in culture or once grafted onto a living host. Certain types of artificial tissues that can be utilized with certain methods of the invention are discussed, for example, in U.S. Pat. Nos. 4,458,678; 4,485,096; and 4,304,866.

Certain methods are performed with human or animal tissue. Thus, the methods can be utilized in various clinical applications for human patients, as well as veterinarian applications. If performed with animals, the animals can be essentially of any kind provided the animal has a tissue layer into which pores can be generated via the application of an electrical signal. Hence, some methods can be performed, for example, with domestic animals such as dogs and cats; farm animals such as horses, cows, sheep and pigs; exotic animals; birds; reptiles; and amphibians, or tissues from these animals. Still other methods are performed with plants or plant cell cultures.

B. AC Signal

1. General

Certain features of the applied AC signal assist in achieving the goal of maintaining a substantially constant electrical state while avoiding some of the problems associated with DC-based methods. For example, a problem with existing DC transdermal iontophoresis technology is that such methods allow skin resistance to vary over time; this in turn results in a variation in the delivery or transport rate of agents through the tissue. The use of an AC signal, however, can reduce this problem. Because the AC component continuously reverses polarity, the tissue remains substantially depolarized throughout the transport procedure and thus is less susceptible to building up charges that may continuously alter the skin structure and interfere with iontophoretic transport.

The AC signal also acts to facilitate transport by inducing the formation of new pores and/or enlarging the existing pores. It has been found by the present inventors that application of an AC signal can generate new pores in tissue without a concomitant enhancement of transport via electroosmosis. Thus, enhanced transport upon application of an AC signal is a consequence, at least in part, of new pore generation. (See, e.g., Li, et al. (1999) *J. Pharmaceutical Sciences* 88:419–427, which is incorporated herein by reference). By generating new pores, application of the AC signal can significantly enhance the rate of transport compared with passive diffusion alone.

Further, while many individuals skilled in the art believe that a DC field is required to transport a charged compound and that an AC signal lacks the necessary driving force for iontophoretic transport, the present inventors have discovered that AC iontophoresis does not eliminate the direct-field effect (i.e., electrophoresis) and about 10% of this effect remains at a relatively low frequency AC (e.g., 10 Hz to 1 kHz). While not intending to be bound by any particular theory, this AC flux-enhancing phenomena is thought to be a result of unsymmetric boundary conditions of the agent across the skin. Thus, an AC signal also provides a means to enhance transport via the reduced direct field effect and electroporation without complications from the electrochemical reactions of the electrodes (e.g. water hydrolysis).

There are other benefits that can be obtained from utilization of an AC signal beyond the enhanced level of controlled delivery. For instance, application of an AC signal during transport, compared to traditional DC iontophoresis, causes less skin irritation and has a higher threshold of sensation. It has been shown that the threshold current for sensation is higher at high AC frequency than for DC. Thus, an AC field for new pore induction in skin during iontophoresis is better than DC for these issues (See, e.g., Dalziel and Mansfield, AIEE Trans, Volume 69, Year 1950, Pages 1162–1168; and Dalziel and Massoglia, AIEE Trans, Volume 75, Year 1956, Pages 49–56.).

These frequency relationships are important for another reason. Results on the frequency effects upon the extent of pore induction in skin show very small dependency of frequency on the extent of pore formation in the low AC frequency region (e.g., 10 to 250 Hz). This result indicates that the effects of frequency upon pore induction in skin is less than those upon the thresholds of sensation. Therefore, an optimal AC frequency region can be utilized in AC methods in which a high AC voltage is employed to increase the extent of pore induction and to enhance transport with minimal sensation and irritation.

2. Applying AC Signal to Tissue

As described in greater detail below, application of the AC signal (and optional prepulse and DC offset signal) is typically applied to a tissue using at least one pair of electrodes that are placed in contact with the tissue being treated. At least one electrode includes a reservoir that contains the agent (e.g., a pharmaceutical agent) that is to be delivered. This electrode is positioned over the region of the tissue through which transport is to occur. A second electrode is also placed in contact with the tissue and is positioned to form a complete electric circuit with a current source. The AC signal can be applied with or without excipients that optimize the conditions for transport of agent(s) across the tissue.

For methods performed with humans, the electrodes are often placed in contact with the outermost skin layer, the stratum corneum. Application of the AC signal, combined with an optional prepulse signal, generates and maintains pores within the skin, thereby allowing agent(s) to be transported across the stratum corneum and into the dermoepidermal layer.

The applied AC signal is of an appropriate voltage and waveform to effectively induce and/or maintain a desired electrical state, which state is an electroporated state that allows for enhanced transport of the agent relative to unporated tissue. Typically, the target electrical state is a selected electrical resistance or electrical conductance. Alternatively, or in addition, other electrical parameters from which electrical resistance or conductance values can be determined can be monitored, as well as any other parameters that correspond to the degree of tissue permeability. Typically, the AC signal is applied to maintain the substantially constant electrical state throughout the time period during which transport of agent is occurring. The actual period for delivery varies significantly depending upon the nature of the application. Some applications can be performed in less than 10 minutes, while other applications may last 12 hours to 24 hours or more.

During the treatment, the AC signal is varied as needed to maintain the electrical state at a selected target value, or more typically, within a target range. Most typically this is achieved by varying the amplitude and/or frequency of the applied voltage. For methods in which electrical resistance of a patient's skin is monitored, the target resistance may vary somewhat from individual to individual. In general, however, the target resistance tends to be approximately 1–30 k$\Omega$·cm$^2$, and more typically a value within the range of 5–15 k$\Omega$·cm$^2$.

The AC signal is typically applied as necessary to maintain the selected target value such that the measured value does not increase or decrease by more than about 20% of the target value. Thus, if the target is 5 k$\Omega$·cm$^2$, then the AC signal is varied as required to keep the measured resistance within the range of about 4–6 k$\Omega$·cm$^2$. In certain other methods, the fluctuation is limited to less than 10% of the target value, in other methods, less than about 5%, and in still other methods, less than about 1%.

The frequency, waveform and duration of the AC signal can vary as long as it is effective to maintain the selected electrical state within the desired range. In general, however, the frequency of the AC signal tends to be at least about 1 Hz. In certain methods, the applied frequency generally falls within the range of about 1 Hz to about 1 kHz; while in other methods, the frequency usually is within the range of about 1 kHz to about 10 kHz. In yet other methods, the frequency usually is within the range of 10 kHz to 30 kHz, or 30 kHz to 200 kHz. The actual frequency can be any particular value or range of values within these ranges. Typical voltages during in vivo human experiments are from about 0 to 40 V although a more practical region is from 0 to 20 V. A variety of waveforms can be utilized. Suitable waveforms include both symmetric and asymmetric waveforms, including waveforms having square, triangular, sinusoidal, saw-tooth and trapezoidal shapes and the like.

The size of the region of the tissue to which a signal is applied can vary significantly depending upon the nature of the application. In general, the region being electroporated and through which agent is transported tends to be from less than 1 cm$^2$ to greater than about 200 cm$^2$. The size of the region tends to be smaller in other applications, ranging from about 5 cm$^2$ to greater than 100 cm$^2$. In still other methods, the region tends to be about 5 cm$^2$ to about 30 cm$^2$.

The size of the region can also be any particular value within these ranges. The shape of the region can be any geometric shape and is not limited to any one particular shape or type of shape.

3. Transport of Neutral Species

Some methods utilizing AC signals to effectuate transport without a DC component can be useful for driving a neutral agent across a tissue. The inventors of the present invention have also found that methods conducted using AC signals at frequencies above about 1 Hz without the application of DC involve little or no electroosmosis. Thus, when performing delivery utilizing only an AC signal, there is negligible electroosmosis. Furthermore, when transporting a neutral agent, there is no electrophoresis. Transport in this situation is similar to passive diffusion but is enhanced due to the induction of new pores (i.e., higher skin porosity) and/or enlarged or increased porosity due to electroporation. Although transport of neutral agents under AC can result in lower fluxes than with traditional constant current DC systems (due mostly to the absence of electroosmosis), methods using strictly AC signals are nonetheless useful because intra-patient and inter-patient variability associated with variable pore surface charge density is minimized. Additionally, there is no electrostatic partitioning of agents into the skin for neutral permeants.

C. Optional Prepulse

A relatively high-voltage DC or AC prepulse can optionally be applied to the tissue to quickly attain a target electrical state or state of electroporation which is subsequently maintained by adjusting the AC signal. Once the prepulse elicits the desired electrical state, the flux of the agent being delivered can be controlled by maintaining a substantially constant electrical state within the electroporated region (e.g., a substantially constant resistance or conductance). When an AC signal is utilized as a prepulse, this signal can subsequently be utilized to maintain the target electrical state. The AC prepulse can also be followed with a separate AC signal to maintain the target electrical state, typically applied shortly after completion of the prepulse.

While the AC signal alone can be used to reach the desired electrical state, the advantage of using a prepulse is that it can accelerate the process of establishing the target electrical state. The longer time period associated with using strictly an AC signal alone without a prepulse, however, is still preferable over a DC-only protocol since the AC-only protocol still results in a predictable and stable electrical state that promotes constant transport properties for the tissue, which is not the case when applying DC signals alone.

In general, the characteristics of the AC or DC prepulse are selected to be effective to obtain the desired electrical state. Typically, this means that the prepulse signal is applied to reach a target electrical resistance or conductance. The voltage of the prepulse is often in the range of about 1 to about 90 V. In other methods, the voltage is in the range of about 9 to about 30 V. In still other methods, the voltage is about 30 to about 40 V, while in other methods about 40 to about 90 V.

If an AC prepulse is utilized, the AC prepulse can be symmetric or asymmetric. A variety of suitable AC prepulse waveforms can be used, including, but not limited to, a square waveform, a sinusoidal waveform, a saw-tooth waveform, a trapezoidal waveform. The duration of the prepulse is sufficiently long so as to achieve the target electrical state. Duration of the prepulse depends in part upon the voltage of the prepulse. In general, however, the prepulse is typically from less than 1 minute to more than 20 minutes. If a DC prepulse is utilized, it too can be supplied in a variety of waveforms wherein the shape is square, triangular, trapezoidal or saw-tooth, for example. As with an AC prepulse, the prepulse is of sufficient duration to establish the target electrical state.

D. Optional DC Offset Signal

Methods employing an AC signal alone to conduct transport across a tissue involve primarily passive diffusion to achieve transport. As indicated above, however, transport is improved over purely passive transport because the AC signal induces electroporation through which agent can passively diffuse. In addition, the existence of a small direct-field effect associated with AC protocols further enhances the transport of ionic compounds. To promote delivery and accelerate the delivery process, the AC signal can optionally be combined with a DC offset signal. Methods utilizing this combination are sometimes referred to as an "AC plus DC protocol." With this particular combination of signals, the AC signal is utilized primarily to maintain a region of the tissue at a substantially constant electrical state to maintain a level of permeability that enhances transport. The DC offset signal is applied to assist in driving transport of the agent. With such a combination of signals, a stable flux of agent across the tissue can be achieved. This contrasts with conventional methods using only DC signals to effectuate transport in which the flux of agent is often unpredictable and changes with the course of the treatment.

As a general matter, the DC offset signal applied to the tissue is typically effective to maintain a substantially constant rate of delivery of the agent being transferred across the tissue. Thus, the timing and duration of the DC offset signal in general is governed by this goal. The rate at which agent is delivered can be controlled by the electrical resistance or conductance of the tissue and the DC offset voltage or current.

The DC offset signal is often applied essentially simultaneously with application of the AC signal. This timing is appropriate, for example, when a prepulse has already established the desired electrical state. In other methods, however, the DC offset signal is delayed until after the AC signal has been initiated. A delay may be appropriate, for instance, with methods conducted without a prepulse to allow the AC signal to establish the target electrical state. Normally, the voltage of the DC offset signal is in the range of about 0.1 V to about 5 V, while in other methods the voltage is in the range of about 0.1 to about 2.5 V. The current range typically is about 0.01 to 0.5 mA/cm$^2$.

E. Exemplary Methods

The foregoing electrical signals can be coalesced in various combinations to yield a variety of different protocols for administering an agent across a tissue. Exemplary methods follow. While the methods can be conducted with a number of different tissue types and different parameters can be monitored to assess the electrical state of the tissue, often such methods are performed with human tissue and involve monitoring the electrical resistance or conductance of the skin.

1. AC-Only Protocol

Figure 1:
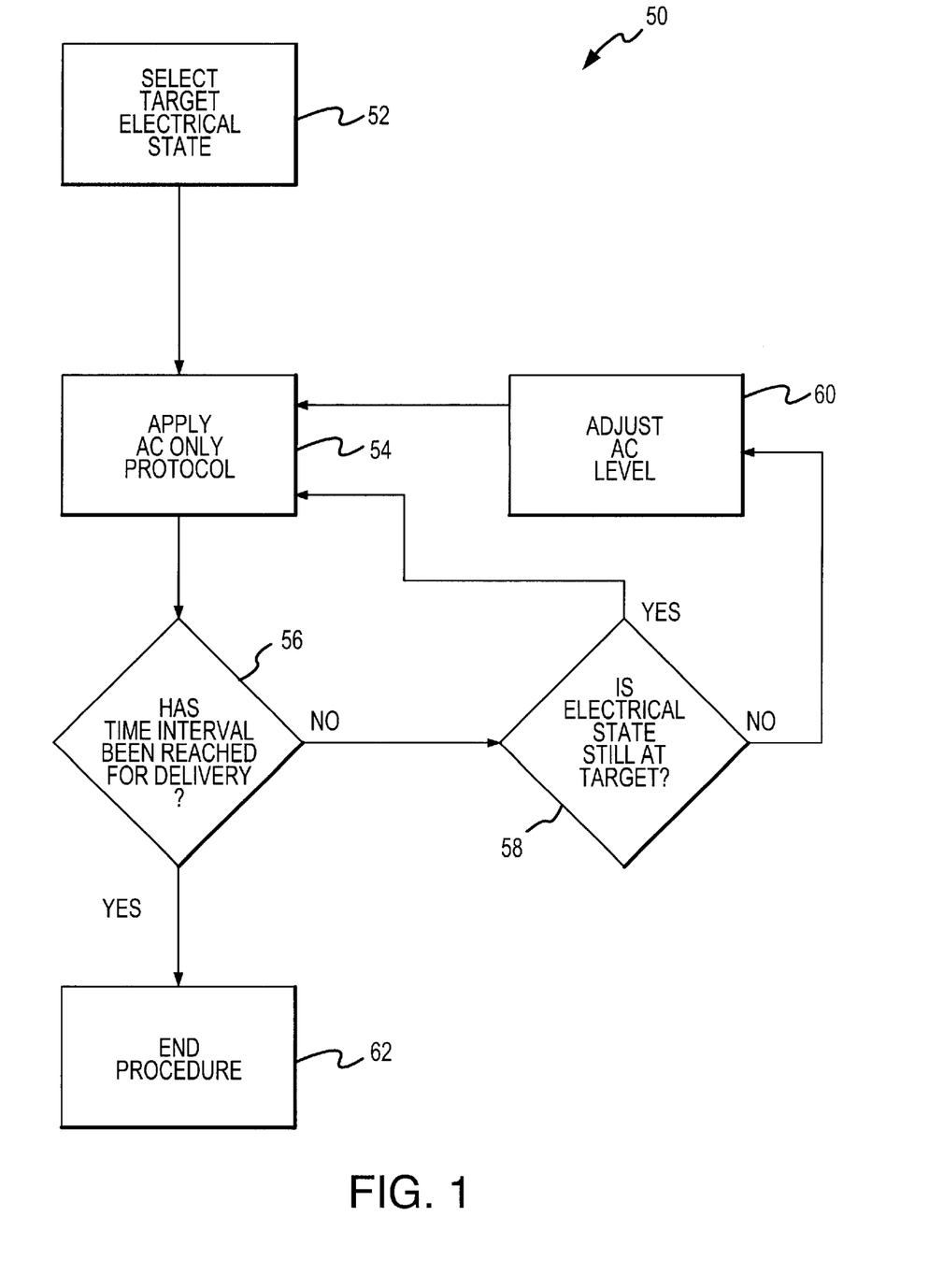
FIG. 1 is a schematic block diagram illustrating steps in a method utilizing only an AC signal to transport an agent across a tissue as provided herein.

FIG. 1 illustrates a method 50 that begins with the selection 52 of a target electrical value or range (e.g., skin resistance or conductance). As indicated supra, the particular target selected can vary somewhat depending upon the individual being treated and the nature of the agent being delivered. An AC signal is subsequently applied 54 to reach the desired target electrical state and to facilitate delivery of the agent across the tissue. As indicated above, application of an AC signal alone without a prepulse may require a longer period of time to reach the desired target. Nonetheless, application of the AC signal significantly increases transport over simple passive diffusion for the reasons discussed supra. Moreover, by reversing the polarity, the AC signal keeps the tissue depolarized and less susceptible to buildup of charged species at the surface of the tissue. The AC signal also maintains a relatively constant level of skin permeability that allows for relatively constant, controlled and predictable delivery of the agent through the tissue.

During the time that the AC signal is applied, the electrical state of the tissue is measured 58, either continuously or periodically, to determine whether the electrical state of the tissue remains within the target range. If the electrical state is within the target range, the AC signals are applied without modification. If, however, the measured electrical state drifts outside the target range, then the AC signal is adjusted 60 to return the electrical state back within the target range. The AC signal is applied for a period sufficient to deliver 56 the desired amount of agent across the tissue at a substantially constant rate. Once the delivery period is complete 56, the treatment ends 62.

2. AC plus Prepulse Protocol

Figure 2:
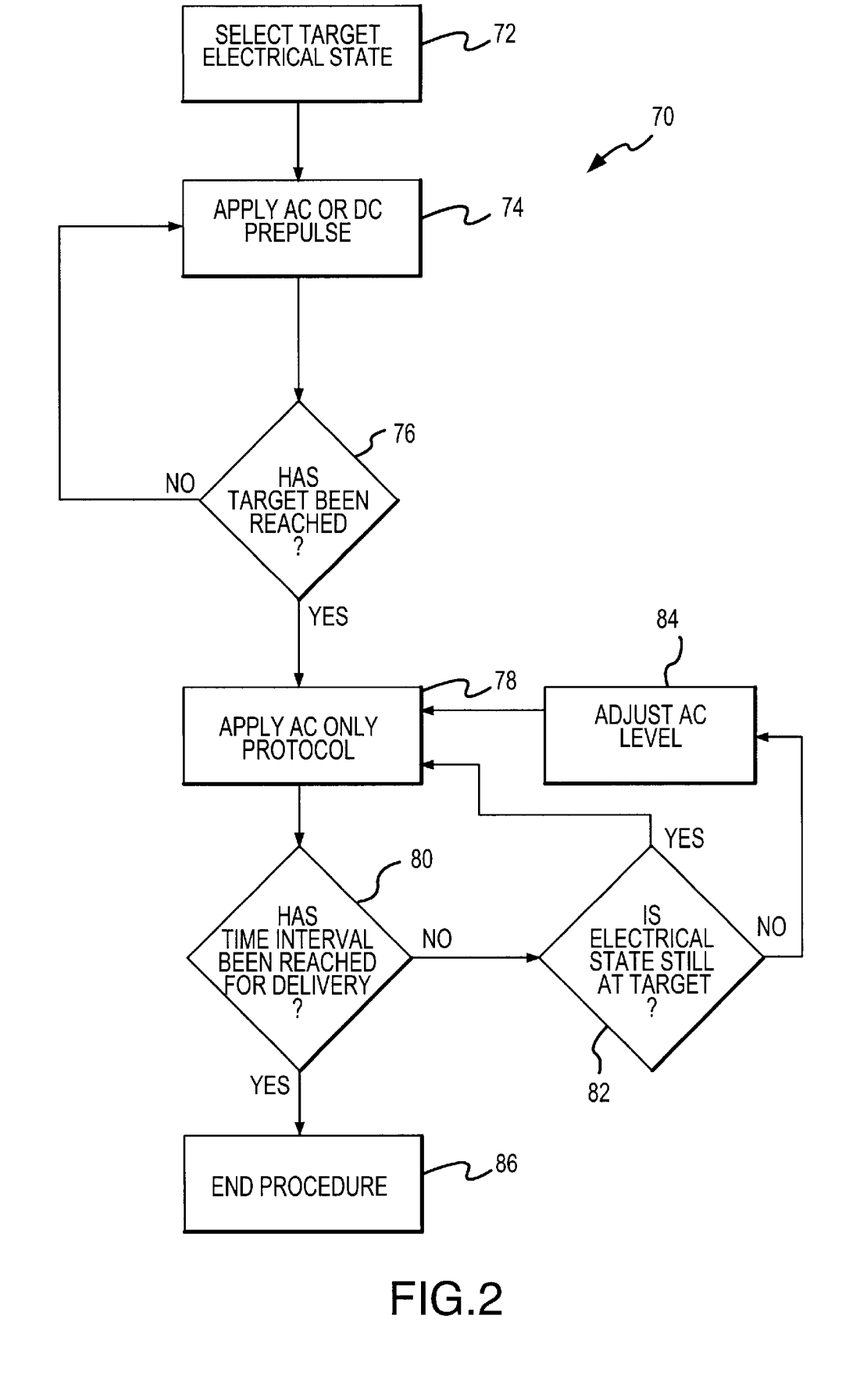
FIG. 2 is a schematic block diagram illustrating steps in a method utilizing an AC signal and a prepulse to transport an agent across a tissue as provided herein.

A schematic illustration of one AC plus prepulse method 70 is set forth in FIG. 2. With this particular approach, the selection 72 of a target electrical state is as described for the AC-only protocol and shown in FIG. 1. However, prior to application 78 of the AC signal, an AC or a DC prepulse is applied 74 to the tissue to relatively quickly achieve the selected electrical state. Once it has been determined that the target state has been reached 76, an AC signal is applied 78 to the tissue. The electrical state is monitored 82 continuously or periodically as described in the preceding section to maintain the target electrical state throughout the time period during which delivery occurs. The AC signal is adjusted 84 as needed to maintain the target state. Once the delivery period is completed 80, the procedure ends 86.

3. AC plus DC Offset

Figure 3:
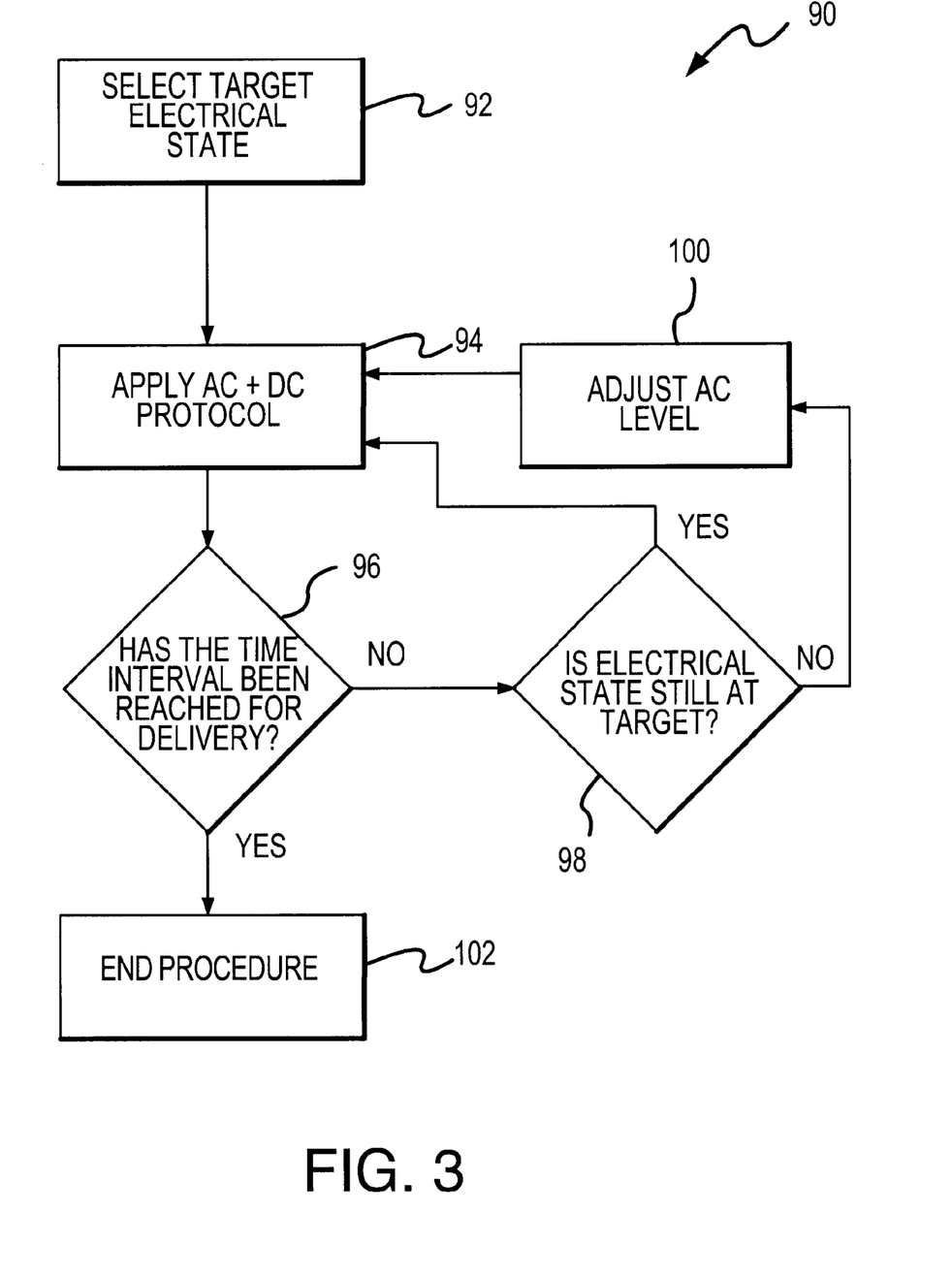
FIG. 3 is a schematic block diagram illustrating steps of a method utilizing an AC signal and a DC offset signal to transport an agent across a tissue as provided herein.

FIG. 3 illustrates the primary aspects of a method 90 utilizing an AC plus DC offset protocol. The initial stages of the method generally track those described for the AC-only protocol including selection 92 of a target electrical state. In this particular method, however, an AC signal and a DC offset signal are applied 94 to the tissue. The DC offset signal can be applied simultaneously with the application of the AC signal or at any time during the treatment. If it is determined 98 that the electrical state is no longer at the targeted value, the AC signal is adjusted 100 to return the electrical state to the target value or range. Such an adjustment is usually independent to the DC signal and does not affect the DC driven transport. The DC signal is typically kept constant but can optionally be adjusted during the application period 94 to change the delivery rate of the agent being transferred. Once a desired amount of agent has been delivered 96 or the time period of treatment has expired, application of the AC and DC signals is terminated 102.

4. AC plus Prepulse plus DC Offset

Figure 4:
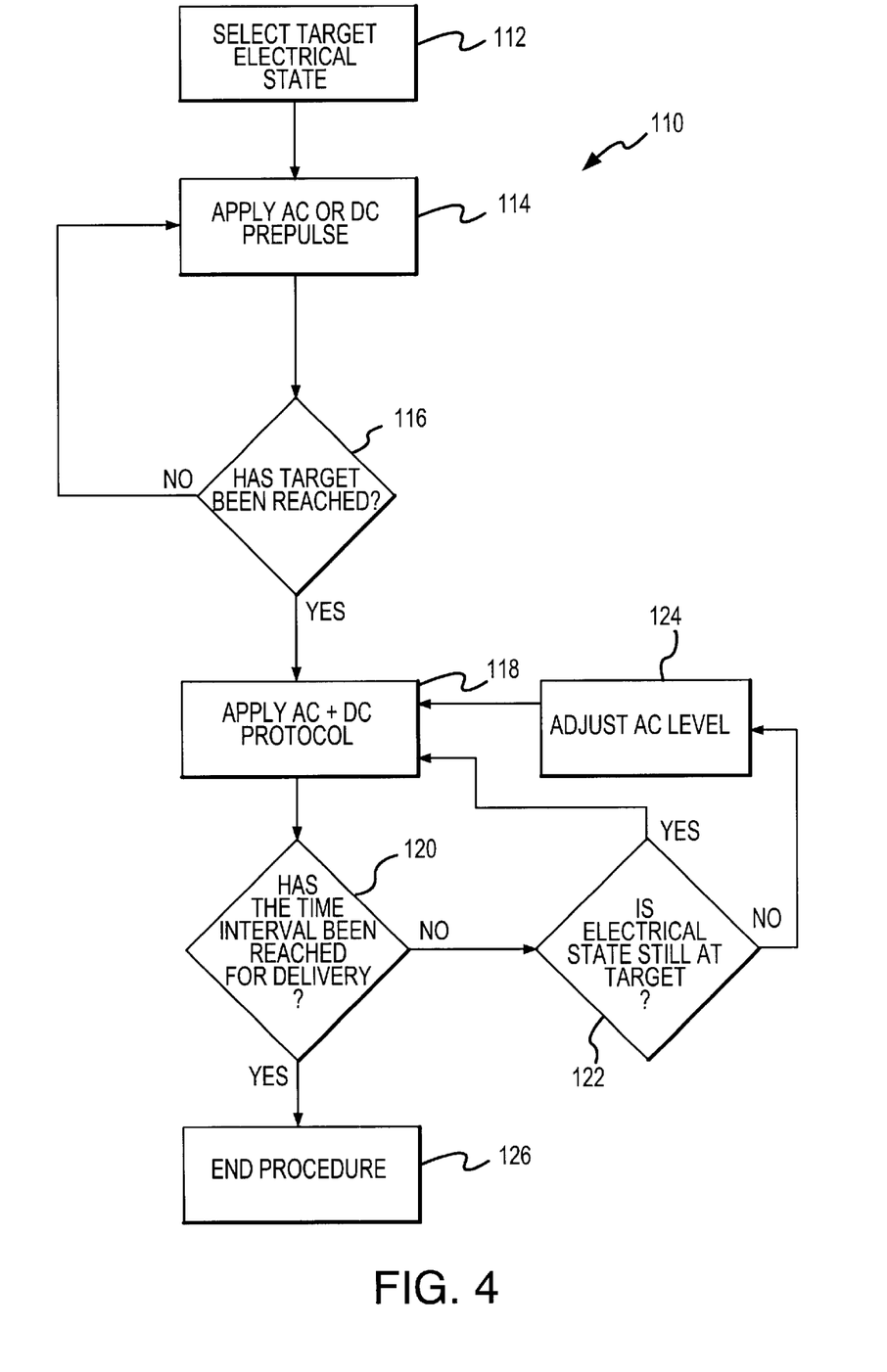
FIG. 4 is a schematic block diagram illustrating steps of one method utilizing a prepulse, an AC signal and a DC offset signal to transport an agent across a tissue as provided herein.

Certain methods 110 combine the prepulse and the DC offset signals with the AC signal (see FIG. 4). Such methods utilize the unique features of each type of signal to optimize delivery of an agent. As described supra, a target electrical state is selected 112 followed by application 114 of an AC or DC prepulse to quickly establish a selected electrical state correlated with an increased level of tissue permeability that promotes transport of the agent. Once it is determined 116 that the target state has been reached, the AC signal and DC offset signal are applied 118, with the AC signal primarily functioning to maintain the target electrical state and the DC offset acting to promote transport of agent across the electroporated tissue. The electrical state is monitored 122. If the electrical state is found to vary from the target, the AC signal is adjusted 124 as required to return the electrical state to the target. Once the treatment time has elapsed 120, the process is completed 126.

F. Agents

The methods disclosed herein can be used in the delivery of a wide range of agents. The methods can generally be utilized to deliver any agent that can be iontophoretically transported across tissue. When the tissue is human skin, then the agent is one that can be moved through electroporated skin.

Often the agent being transported is a pharmacologically active agent that is administered for therapeutic or prophylactic purposes. Examples of such agents include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; antiinfective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; β-agonist; and tocolytic agents.

In some methods, two or more pharmacologically active agents are administered in combination. Further, a pharmacologically active agent can be combined with various agents that enhance certain aspects of transport. For instance, a therapeutic agent can be combined with an agent that improves blood circulation to enhance the rate of delivery of the therapeutic agent throughout a patient's body. Other methods utilize one or more excipients that act to control the level of transport that occurs during the procedure.

The agent can also be part of a formulation and can be combined, for example, with a vehicle suitable for delivery across a tissue. For example, the agent administered can be part of a composition that includes, depending on the formulation desired, pharmaceutically-acceptable, non-toxic carriers or diluents commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the composition or formulation can also include other carriers, adjuvants, or non-toxic, nontherapeutic, non-immunogenic stabilizers, excipients and the like. The compositions may also include additional substances to approximate physiological conditions, such as pH adjusting and buffering agents, tonicity adjusting agents, wetting agents, detergents and the like. Further guidance regarding formulations that are suitable for various types of administration can be found in Remington's Pharmaceutical Sciences, Mack Publishing Company, Philadelphia, Pa. 17th ed. (1985).

If the agent(s) delivered are pharmaceutical agents, then the therapeutic delivered can be administered for prophylactic and/or therapeutic treatments. A therapeutic amount refers to an amount sufficient to remedy a disease state or symptoms, or otherwise prevent, hinder, retard, or reverse the progression of a disease or any other undesirable symptoms. A prophylactic amount is an amount sufficient to prevent, hinder or retard a disease or any other undesirable symptom. The actual amount of an agent required will depend upon a number of factors known to those of skill in the art, including, for example, the potency and potential toxicity of the agent, the stability of the agent in the body, and the size and age of the individual receiving the agent.

The agent can include molecules not delivered for their therapeutic or prophylactic value such as nutrients, metabolites, and dyes, for example.

IV. Delivery Systems

Figure 5:
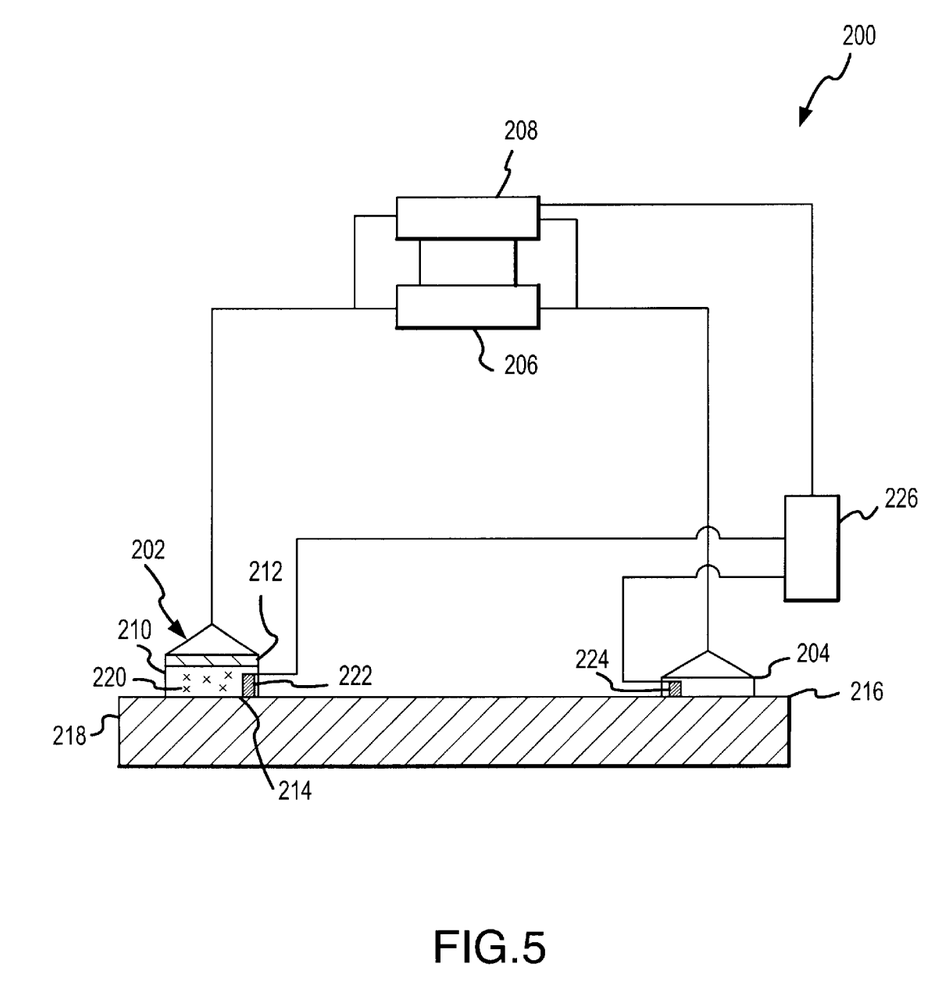
FIG. 5 is a schematic representation of an exemplary apparatus for transporting an agent across a tissue, such as transporting a pharmacologically active agent across the skin of a patient.

One embodiment of an apparatus for performing the methods disclosed herein is represented schematically in FIG. 5. This system 200 for delivering agents across a tissue or body surface 218 generally comprises a first set of two electrodes 202, 204 electrically connected to a power source 206. The power source 206 can be a single source capable of delivering both an AC and a DC signal, or include two separate sources, one for delivering an AC signal and the other that delivers a DC signal. A circuit including the two electrodes 202, 204 and power source 206 is also connected to a controller 208 that monitors the electrical signals delivered to the electrodes 202, 204 and which can send signals to the power source 206 to alter the signals transmitted therefrom.

At least one of the electrodes 202 includes at least one reservoir (e.g., 210) and is electrically connected to a reservoir surface 212. Another surface 214 of the reservoir 210 is placed against a surface 216 of the tissue 218 (e.g., a patient's skin) and held in place, for example, by an adhesive or gel (not shown). The reservoir 210 contains one or more agents (e.g., pharmaceutical agents) 220 that are to be delivered across the tissue 218. The reservoir 210 can be a chamber that houses a solution into which the agent(s) 220 is/are dissolved. Alternately, the reservoir 210 can include a porous material that retains a solution, paste or gel containing the agent(s) 220 to be delivered. Various other reservoir systems known to those of skill in the art can also be utilized. The other electrode 204 of the pair is also placed in contact with a surface 216 of the tissue 218 and held in position with an adhesive or gel (not shown). This electrode 204 is positioned to allow for formation of a current that flows between the two electrodes 202, 204. DC offset current can be applied to drive transport of a charged agent within the reservoir 210 across the tissue 218 toward the electrode of opposite charge. Uncharged agents are driven from the anode (the positive electrode) across the tissue 218 at physiological pH by electroosmosis.

The apparatus 200 includes a second set or monitoring set of electrodes 222, 224 that are placed within the region of the tissue being electroporated to monitor the electrical state of the tissue 218 during transport of the agent across the tissue. As indicated supra, the electrical state monitored is one that reflects the extent of tissue permeability or the state of electroporation (e.g., electrical resistance or electrical conductance). The monitoring electrodes 222, 224 can be separate from the first set of electrodes 202, 204, although this is not required, since the first set of electrodes 202, 204 can be used to monitor the electrical state of the tissue 218. The monitoring electrodes 222, 224 can be attached to a separate monitor 226 as shown in FIG. 5, or optionally to the same controller 208 as the first set of electrodes 202, 204. If attached to a separate monitor 226, monitor 226 can send signals regarding the electrical state of the tissue 218 as measured by the second set of electrodes 222, 224 to controller 208.

The first set of electrodes 202, 204 utilized in applying the electrical signals can be of any of the standard types of electrodes utilized in iontophoresis. Some systems use non-polarizable electrodes such as standard electrocardiograph electrodes manufactured from silver/silver chloride. Other suitable materials include gold, stainless steel and platinum. Multichannel dispersive electrodes can also be utilized in certain methods (see, e.g., U.S. Pat. No. 5,415,629).

When a DC offset signal is utilized, the electrode including the reservoir functions as either the cathode or anode depending upon the charge of the agent being delivered. In general, the anode receives the positive contribution of the DC offset signal, whereas the cathode receives the negative contribution of the DC offset signal. Consequently, if a DC offset signal is applied, positively charged ions are driven into the tissue at the anode and negatively charged ions are driven across the tissue at the cathode. At physiological pH, neutral agents are driven by electroosmosis into the tissue from the anode. When a DC offset is not utilized and only an AC signal is delivered, there is no formal anode or cathode.

In some systems, it can be useful to include a reservoir at both electrodes 202, 204. For example, if only an AC signal is applied, agent can be transported via diffusion from either reservoir. As described further infra, some methods using a DC offset involve reversing the direction of current flow at different time points. Reservoirs located at both electrodes 202, 204 can be useful in such methods because delivery can occur from both reservoirs depending upon the direction of the DC signal. Two reservoirs can also be utilized to good effect if two different agents of opposite charge are to be delivered. In such instances, differently charged agents are placed in separate reservoirs so that delivery can proceed simultaneously from both reservoirs.

In operation, the reservoir 210 is filled with a solution or matrix that includes the agent 220 to be transferred. If the reservoir 210 includes an absorbent material, this is soaked with a solution containing the agent or coated with a paste or gel containing the agent. Once the first set of electrodes 202, 204 has been properly positioned, an electrical signal is delivered to the first set of electrodes 202, 204 via the power supply 206. The particular signals delivered depend upon which of the protocols disclosed supra are utilized. In general, however, the various methods involve utilizing the power supply 206 to generate an AC signal of appropriate shape, duration, frequency and voltage to maintain a selected electrical state. If during the transport process, the electrical state deviates from the target electrical state as detected by the monitoring electrodes 222, 224, then the appropriate adjustments are made with the power supply 206 to vary the AC signal such that the electrical state is brought back to the target value or within the target range.

The controller 208 can be under microprocessor control. If the microprocessor-based controller determines on the basis of signals from the monitoring electrodes 222, 224 that the electrical state has deviated from the target, it can signal the power source 206 to alter the AC signal so as to return the electrical state to the desired target. Such a controller can also include a safety shut off if it is determined that the electrical state of a patient's skin, for example, has reached a potentially dangerous level.

For methods utilizing either an AC or a DC prepulse, a prepulse of appropriate frequency, voltage and duration is generated by the power source 206 that is effective to reach the target electrical state. The monitoring electrodes 222, 224 can be utilized during this process to follow the progress towards the desired electrical state. Once this state is achieved, a signal is sent to the controller 208 which terminates generation of the prepulse and then generates the AC signal and/or the DC offset for application to the tissue.

As indicated above, in some methods the concentration of the agent 220 within the reservoir 210 is sufficiently higher than that on the other side of the tissue such that agent is transported through the electroporated region via passive diffusion. More typically, however, the power supply 206 is also utilized to generate a DC offset signal. This current drives the transport of a charged agent towards the electrode having an opposite charge or a neutral agent from the anode to cathode via electroosmosis. In some procedures, the direction of the DC offset current flow can be reversed between the first set of electrodes to maximize the use of both electrodes and avoid the generation of unwanted ions/products in the electrodes.

Through the use of solid-state circuitry, the various foregoing elements such as signal delivering electrodes, power supply and reservoir can be included in a small, integrated device that can be conveniently worn by an individual without interfering with the individual's daily activities.

V. Exemplary Applications

The transport methods provided herein can be used in a variety of applications, including the treatment of various disorders and diseases. Certain methods are used in the treatment of diabetes and various weight disorders such as obesity, for example. In the case of diabetes, the methods can be utilized for the controlled delivery of insulin or other hypoglycemic agent when the glucose level of an individual is elevated and in the transport of glucagon or carbohydrate (e.g., glucose) into an individual that is hypoglycemic. Weight loss treatments can involve the delivery of appetite suppressors such as cholecystokinin, for example.

Related methods are performed to assist in treating individuals seeking to recover from narcotic or other types of substance abuse. These methods can involve, for example, the administration of agents that assist in the detoxification process. The delivery methods also find value in treating nicotine addiction. Treatment of nicotine addiction often involves a program in which decreasing levels of nicotine are delivered over the treatment period. Detoxification methods generally involve delivery of an agent that blocks the effect of, or substitutes for, the substance being abused.

Certain methods lend themselves well to the treatment of various blood circulation and pressure disorders. For example, the methods can be used in the transport of various anticoagulants (e.g., heparin, low molecular weight heparin analogues, and warfarin sodium). Such methods can be useful in prevention of stroke and/or in the reducing clotting risk following certain surgical procedures. Treatment of blood pressure disorders is effected by the delivery of appropriate levels of blood pressure medicines (e.g. $\alpha$-Blockers & $\beta$Blockers). Some methods find value in pain management. Such methods involve the transport of various narcotics to control pain during surgery or in the management of the extreme pain experienced by certain individuals suffering from various debilitating diseases. Yet other methods find value in delivering drugs for psychiatric disorders, sleep disorders, movement disorders (e.g. Parkinson's disease), infections, and local and diffuse inflammatory disorders.

Still other methods are directed towards various dermatological treatments. Thus, certain methods involve the delivery of agents appropriate for treating skin conditions such as acne, eczema and psoriasis. Some methods involve the delivery of agents that hydrate the skin such as in cosmetic applications. Conversely, agents that inflame the skin can be delivered to result in the peeling of an external layer of skin, thereby stimulating the activation of various collagen growth factors and the growth of new skin layers.

The following example is provided to illustrate certain aspects of the methods disclosed herein and is not to be construed so as to limit the scope of the methods.

EXAMPLE

I. Experimental

A. Materials

Radiolabeled [$^3$H] mannitol and [$^{14}$C] tetraethylammonium bromide (TEA$^+$) were purchased from New England Nuclear (Boston, Mass.) and American Radiolabeled Chemicals (St. Louis, Mo.). Human epidermal membrane (HEM) was prepared by heat separation of split-thickness excised human skin. Phosphate buffered saline (PBS) (pH 7.4) was prepared at ionic strength of 0.1 M using reagent grade chemicals and deionized water.

B. Experimental Methods

1. General

Iontophoresis studies were carried out in a side-by-side two-chamber diffusion cell (diffusional surface area of around 0.8 cm$^2$ and chamber volume of 2 mL) with HEM at 37° C. The apparent permeability coefficients (P) in each experiment were calculated by:

$$P = \frac{1}{C_D A} \frac{dQ}{dt} \quad (1)$$

where A is the membrane surface area, t is time of treatment, Q is the amount of permeant transported into the receiver chamber, and $C_D$ is the concentration of permeant in the donor chamber. The pH of the solutions in the donor and receiver chambers was checked after each iontophoresis run.

2. Constant Current Methods

Experiments were carried out at 0.13 mA/cm$^2$, using a constant current iontophoretic device (phoresor II Auto, Model No. PM 850, Iomed, Inc., Salt Lake City, Utah) with Ag—AgCl as the electrodes. HEM initial resistance was measured by applying 100 mV electrical potential across the membrane using a four electrode potential system (JAS Instrumental System, Inc., Salt Lake City, Utah), as previously described by Srinivsan, et. al, (1989) Journal of Controlled Releases;10:157–165. HEM resistance during the iontophoresis was measured by monitoring the electrical potential drop across the membrane using two flexible Luggin capillaries that were inserted into the donor and receiver compartments of the diffusion cells. Each of the Luggin capillaries contained a calomel electrode that was connected to a voltmeter and/or an oscilloscope (model 2211, Tektronix Inc., Beaverton, Oreg.). The HEM resistance during iontophoresis thus could be determined according to the output current level and the voltmeter readings.

Trace amounts of [$^{14}$C] TEA$^+$ (triethylammonium) and [$^3$H] mannitol were added to the donor chamber at the beginning of the experiment. One ml of sample was taken from the receiver chamber approximately every 30 minutes and replaced with fresh PBS. A 10 $\mu$l sample was taken from the donor chamber every hour. Samples were mixed with 10 ml scintillation cocktail (Ultima Gold™, Packard Instrument Co., Meriden, Conn.) and assayed by a dual-labeled liquid scintillation counter (Parkard TriCarb™ Model 1900 TR Liquid Scintillation Analyzer).

3. AC+DC Offset Methods 5 volts DC was applied using the four electrode potentiostat system to reduce the skin electrical resistance to 2 k$\Omega$, followed by a 50 Hz square-wave AC with 250 mV DC offset generated from a function generator (Model 45011, BK Precision, Placentia, Calif.). The output AC voltage was manually adjusted between 3 to 8 volts to keep the skin resistance at 2 k$\Omega$(±10%) during the entire period of the experiment. The same permeants and sampling protocol were used as described in the Constant Current Session.

4. AC+Passive Transport Methods (AC without DC Offset)

The same protocol was used to reduce the skin electrical resistance to 2 k$\Omega$ as described in the AC+DC Offset method protocol. The DC pulse was followed by a 50 Hz square-wave AC without the DC offset to keep the skin resistance at 2 k$\Omega$(±10%) by manually adjusting the output AC voltage as described in the AC+DC Offset experiment session. Permeants and sampling protocol were the same as in the Constant Current and AC+DC Offset sessions as described above.

II. Results

A. Comparison of Traditional Constant Current DC Methods, AC+DC Offset and AC without DC Offset Protocols The permeability coefficient (flux normalized by the donor concentration) of mannitol and TEA$^+$ through a human epidermal membrane was determined for a number of different samples according to the constant current DC method, the AC without DC Offset protocol, and the AC+DC Offset protocol set forth in section I of this example. Mean values and standard deviation values were calculated from the results and are summarized in Tables 1 and 2 below.

The standard error of the means (SEM) indicates the amount of variability in the measured permeability values for each approach, and more specifically is the percentage of the mean that the standard deviation represents. Hence, the smaller the SEM, the smaller the sample variability (standard deviation) normalized to the mean and the less variability in the measured values.

As Table 1 shows, the traditional constant current DC protocol produced relatively large SEM values for mannitol transport as compared to the SEM values for the new AC without DC Offset method and AC+DC Offset method. In addition, Table 2 demonstrates TEA$^+$ transport. Like mannitol transport, Table 2 shows the relatively large SEM value for traditional constant current DC method compared with the AC without DC Offset method or the AC+DC Offset method.

These results indicate that a significant reduction in variability of the electrical state of the tissue as measured by the permeability values was achieved utilizing either the AC without DC Offset or the AC+DC Offset methods for both uncharged permeants, such as mannitol, and charged permeants, such as TEA$^+$. Further, since these data represent the variability between skin samples from different human donors, we have demonstrated the superiority of AC without DC Offset or AC+DC Offset iontophoresis, for controlling inter-patient variability.

Table 3 below depicts the effect of various current profiles on the transport of mannitol and TEA$^+$. The last column of Table 3 shows the slope of the linear regression line of the best-fit line for all transport data points between 100 and 330 minutes. The slope of a line is defined as the rate of change of the relationship between two variables, in this case, permeant flux and time. Therefore, a slope of zero indicates that permeant flux is not changing with respect to time and the more positive (or negative) the flux, the more the flux is changing with time.

Table 3 shows that the change in flux with AC is roughly the same whether the target skin resistance is 2 or 4 k$\Omega$ for both the uncharged mannitol and the cationic TEA$^+$. It is also clear that the rate of change of the mannitol flux is 57% lower with AC+DC Offset protocol compared with an AC without DC Offset protocol. The rate of change of mannitol flux with the traditional constant current DC was 5.7- and 10-fold higher than the AC without DC Offset method and the AC+DC Offset method, respectively. The rate of change of normalized TEA$^+$ flux was 7-fold higher with the AC+DC Offset method than the AC without DC Offset method. Lastly, the rate of change of the normalized TEA$^+$ flux was 3- and 20-fold higher with traditional constant current DC only than with the AC+DC Offset protocol and AC without DC Offset protocol, respectively.

All of this data demonstrates that AC and AC+DC iontophoresis produces less inter-subject variability (Tables 1 and 2) and less intra-subject variability (Table 3) than traditional constant current DC iontophoresis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

TABLES

TABLE 1

Mannitol transport data. Mean and standard deviation represent permeability coefficient.

|  | 0.13 mA/cm² DC | AC (50 Hz) w/o DC Offset, target skin resistance = 2 kΩ | AC (50 Hz) with 0.25 V DC offset, target skin resistance = 2 kΩ |
|---|---|---|---|
| ONE TIME POINT (180 MIN) | | | |
| Number of samples | 7 | 4 | 6 |
| Mean | $1.5 \times 10^{-7}$ cm/s | $1.01 \times 10^{-7}$ cm/s | $1.7 \times 10^{-7}$ cm/s |
| Standard deviation | $0.9 \times 10^{-7}$ cm/s | $0.35 \times 10^{-7}$ cm/s | $0.2 \times 10^{-7}$ cm/s |
| Standard error of the mean | 61.3% | 34.8% | 8.8% |
| ALL DATA POINTS FROM 100 TO 330 MIN | | | |
| Number of data points (Number of samples) | 42 (7) | 28 (4) | 36 (6) |
| Mean | $1.6 \times 10^{-7}$ cm/s | $9.85 \times 10^{-8}$ cm/s | $1.6 \times 10^{-7}$ cm/s |
| Standard deviation | $1.0 \times 10^{-7}$ cm/s | $2.68 \times 10^{-8}$ cm/s | $0.3 \times 10^{-7}$ cm/s |
| Standard error of the mean | 60.6% | 27.2% | 18.8% |

TABLE 2

TEA⁺ transport. Mean and standard deviation represent permeability coefficient.

|  | 0.13 mA/cm² DC | AC (50 Hz) w/o DC Offset, target skin resistance = 2 kΩ | AC (50 Hz) with 0.25 V DC offset, target skin resistance = 2 kΩ |
|---|---|---|---|
| ONE TIME POINT (180 MIN) | | | |
| Number of samples | 8 | 4 | 7 |
| Mean | $4.7 \times 10^{-6}$ cm/s | $9.9 \times 10^{-7}$ cm/s | $6.2 \times 10^{-6}$ cm/s |
| Standard deviation | $1.8 \times 10^{-6}$ cm/s | $7 \times 10^{-8}$ cm/s | $1.0 \times 10^{-6}$ cm/s |
| Standard error of the mean | 38.3% | 6.8% | 16.1% |
| ALL DATA POINTS FROM 100 TO 330 MIN | | | |
| Number of data points (Number of samples) | 48 (8) | 28 (4) | 42 (7) |
| Mean | $4.7 \times 10^{-6}$ cm/s | $1.08 \times 10^{-6}$ cm/s | $6.0 \times 10^{-6}$ cm/s |
| Standard deviation | $1.7 \times 10^{-6}$ cm/s | $2.4 \times 10^{-7}$ cm/s | $9 \times 10^{-7}$ cm/s |
| Standard error of the mean | 36.2% | 22.5% | 15.0% |

TABLE 3

Normalized flux data for mannitol and TEA⁺.

| Current Type | AC Frequency | DC Offset | Target Skin Resistance | Slope (cm sec⁻¹ min⁻¹) |
|---|---|---|---|---|
| NORMALIZED MANNITOL FLUX | | | | |
| AC | 50 Hz | — | 2 kΩ | $7 \times 10^{-11}$ |
| AC | 50 Hz | — | 4 kΩ | $7 \times 10^{-11}$ |
| AC + DC | 50 Hz | 250 mV | 2 kΩ | $4 \times 10^{-11}$ |
| DC | — | 0.13 mA/cm² | — | $4 \times 10^{-10}$ |
| NORMALIZED TRIETHYLAMMONIUM (TEA+) FLUX | | | | |
| AC | 50 Hz | — | 2 kΩ | $3 \times 10^{-10}$ |
| AC | 50 Hz | — | 4 kΩ | $-3 \times 10^{-10}$ |
| AC + DC | 50 Hz | 250 Mv | 2 kΩ | $2 \times 10^{-9}$ |
| DC | — | 0.13 mA/cm² | — | $6 \times 10^{-9}$ |

What is claimed is:

1. A method of delivering an agent across a tissue, comprising.
    (a) supplying one or more electrical signals, the one or more electrical signals comprising an AC signal;
    (b) applying the AC signal to the tissue; and
    (c) adjusting the AC signal so as to maintain a substantially constant electrical state within a region of the tissue, wherein maintenance of the substantially constant electrical state facilitates delivery of the agent.

2. The method of claim 1, wherein the AC signal is adjusted to maintain a substantially constant state of electroporation in the region of the tissue throughout the time period in which the agent is delivered.

3. The method of claim 1, wherein the electrical state is electrical conductance or electrical resistance and the AC signal is adjusted to maintain a substantially constant electrical conductance or electrical resistance in the region of the tissue throughout the time period in which the agent is delivered.

4. The method of claim 1, wherein the waveform of the AC signal is symmetric.

5. The method of claim 1, wherein the waveform of the AC signal is asymmetric.

6. The method of claim 1, wherein the waveform of the AC signal is a square-waveform, a sine-waveform, a saw-tooth waveform, or trapezoidal waveform.

7. The method of claim 1, wherein the frequency of the AC signal is at least about 1 Hz.

8. The method of claim 1, wherein the frequency of the AC signal is in the range of about 1 Hz to about 1 kHz.

9. The method of claim 7, wherein the frequency of the AC signal is in the range of about 1 kHz to about 10 kHz.

10. The method of claim 7, wherein the frequency of the AC signal is in the range of about 10 kHz to 30 kHz.

11. The method of claim 1, wherein the one or more electrical signals comprise an electrical prepulse applied to the tissue prior to the AC signal to induce electroporation within the region.

12. The method of claim 1, wherein the voltage of the electrical prepulse is in the range of about 1 to about 90 V.

13. The method of claim 12, wherein the voltage of the electrical prepulse is in the range of about 9 to about 30 V.

14. The method of claim 12, wherein the voltage of the electrical prepulse is in the range of about 30 to about 40 V.

15. The method of claim 12, wherein the voltage of the electrical prepulse is in the range of about 40 to about 90 V.

16. The method of claim 12, wherein the electrical prepulse is a DC prepulse.

17. The method of claim 12, wherein the electrical prepulse is an AC prepulse.

18. The method of claim 12, wherein the electrical prepulse is a DC prepulse.

19. The method of claim 12, wherein the electrical prepulse is an AC prepulse.

20. The method of claim 1, wherein delivery of the agent is via passive diffusion through the electroporated region.

21. The method of claim 1, wherein:.
(a) the one or more electrical signals further comprise a DC offset signal; and
(b) applying comprises applying the DC signal to the tissue, wherein the DC offset signal is effective to promote delivery of the agent through the region.

22. The method of claim 21, wherein the DC offset signal is applied substantially continuously during delivery of the agent and is of a voltage or current effective to control the rate of delivery of the agent through the region.

23. The method of claim 21, wherein the voltage of the DC offset signal is in the range of about 0.1 V to about 5 V and the current range is about 0.01 to 0.5 mA/cm$^2$.

24. The method of claim 21, wherein the AC signal and the DC offset signal are provided simultaneously.

25. The method of claim 21, wherein the DC offset signal is applied after initiation of the AC signal.

26. The method of claim 21, wherein the DC offset signal is applied utilizing two electrodes in contact with the tissue and the direction of current flow of the DC offset signal is periodically reversed between the two electrodes.

27. The method of claim 1, wherein:
(a) the one or more electrical signals further comprise an electrical prepulse and a DC offset signal;
(b) applying comprises
(i) applying the electrical prepulse to the tissue prior to the AC signal to induce electroporation within the region; and
(ii) applying the DC offset signal to the tissue, wherein the DC offset signal is effective to promote delivery of the agent through the region.

28. The method of claim 27, wherein the voltage of the electrical prepulse is in the range of about 1 to about 90 V.

29. The method of claim 28, wherein the electrical prepulse is a DC prepulse.

30. The method of claim 28, wherein the electrical prepulse is an AC prepulse.

31. The method of claim 27, wherein the DC offset signal is applied utilizing two electrodes in contact with the tissue and the direction of current flow of the DC offset signal is periodically reversed between the two electrodes.

32. The method of claim 27, wherein the DC offset signal is applied substantially continuously during delivery of the agent and is of a voltage or current effective to maintain a substantially constant rate of delivery of the agent through the region.

33. The method of claim 27, wherein the conductance or resistance within the region is maintained within a range that is approximately 20% of a target conductance or resistance.

34. The method of claim 33, wherein the range is approximately 10% of the target conductance or resistance.

35. The method of claim 34, wherein the range is approximately 5% of the target conductance or resistance.

36. The method of claim 35, wherein the range is approximately 1% of the target conductance or resistance.

37. The method of claim 1, wherein the human tissue is skin.

38. The method of claim 1, wherein the human tissue is mucosal membrane.

39. The method of claim 1, wherein the tissue is an animal tissue other than a human tissue.

40. The method of claim 1, wherein the tissue is a plant tissue.

41. The method of claim 1, wherein the region has an area in the range of about 1 cm$^2$ to about 200 cm$^2$.

42. The method of claim 41, wherein the region has an area in the range of about 5 cm to about 100 cm$^2$.

43. The method of claim 42, wherein the region has an area in the range of about 5 cm to about 30 cm$^2$.

44. The method of claim 1, wherein the agent is a pharmacologically active agent.

45. The method of claim 44, wherein the pharmacologically active agent is selected from the group consisting of analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; β-agonist; a tocolytic agent; and combinations thereof.

46. The method of claim 45, wherein the pharmacologically active agent is a pharmacologically active metabolite of the pharmacologically active agent.

47. The method of claim 45, wherein the pharmacologically active agent is contained in a liquid formulation comprising a vehicle suitable for transdermal drug delivery.

48. The method of claim 45, wherein the pharmacologically active agent comprises two or more pharmacologically active agents administered in combination.

49. The method of claim 1, wherein the agent is a nucleic acid.

50. A method of delivering an agent across a human tissue, comprising.
(a) supplying one or more electrical signals, the one or more electrical signals comprising an AC signal;
(b) applying the AC signal to the human tissue, wherein the tissue is human skin or mucosal tissue; and
(c) adjusting the AC signal so as to maintain a substantially constant state of electroporation within a region of the tissue, wherein maintenance of the substantially constant state of electroporation facilitates delivery of the agent.

51. The method of claim 50, further comprising applying an electrical prepulse to the tissue prior to the AC signal to induce electroporation within the region.

52. The method of claim 50, further comprising applying a DC offset signal effective to promote delivery of the agent through the region to the tissue.

53. The method of claim 51, further comprising applying a DC offset signal effective to promote delivery of the agent through the region to the tissue.

* * * * *

UNITED STATES PATENT AND TRADEMARK OFFICE
CERTIFICATE OF CORRECTION

PATENT NO. : 6,512,950 B2
DATED : January 28, 2003
INVENTOR(S) : S. Kevin Li et al.

It is certified that error appears in the above-identified patent and that said Letters Patent is hereby corrected as shown below:

Column 2,
Line 44, "bums" should read -- burns --.

Column 18,
Line 49, "lontophoresis" should read -- Iontophoresis --.

Column 22,
Line 16, "comprising." should read -- comprising: --.

Column 23,
Line 3, "wherein:." should read -- wherein: --.

Column 24,
Lines 4 and 6, each occurrence of "5 cm" should read -- 5 cm$^2$ --.

Signed and Sealed this

Nineteenth Day of August, 2003

JAMES E. ROGAN
*Director of the United States Patent and Trademark Office*